US008530152B2

(12) United States Patent
Mehra et al.

(10) Patent No.: US 8,530,152 B2
(45) Date of Patent: Sep. 10, 2013

(54) METHODS OF REDUCING NON-SPECIFIC INTERACTION IN METAL NANOPARTICLE ASSAYS

(75) Inventors: Rajesh K. Mehra, Sunnyvale, CA (US); Vincent Chiang, San Ramon, CA (US); Kenneth Aron, Burlingame, CA (US)

(73) Assignee: Abaxis, Inc., Union City, CA (US)

( * ) Notice: Subject to any disclaimer, the term of this patent is extended or adjusted under 35 U.S.C. 154(b) by 800 days.

(21) Appl. No.: 12/500,549

(22) Filed: Jul. 9, 2009

(65) Prior Publication Data

US 2010/0120057 A1 May 13, 2010

Related U.S. Application Data

(60) Provisional application No. 61/079,777, filed on Jul. 10, 2008.

(51) Int. Cl.

| | |
|---|---|
| ***C12Q 1/70*** | (2006.01) |
| ***C12Q 1/68*** | (2006.01) |
| ***G01N 33/53*** | (2006.01) |
| ***G01N 33/553*** | (2006.01) |
| ***G01N 33/566*** | (2006.01) |
| ***G01N 33/569*** | (2006.01) |
| ***G01N 33/573*** | (2006.01) |

(52) U.S. Cl.
USPC .................. 435/5; 435/6.1; 435/7.1; 435/7.2; 435/7.21; 435/7.32; 435/501; 435/525

(58) Field of Classification Search
None
See application file for complete search history.

(56) References Cited

U.S. PATENT DOCUMENTS

| | | | |
|---|---|---|---|
| 4,313,734 | A | 2/1982 | Leuvering |
| 5,102,788 | A | 4/1992 | Cole |
| 5,304,465 | A | 4/1994 | Garland |
| 5,641,640 | A | 6/1997 | Hanning |
| 5,905,028 | A | 5/1999 | Frame |
| 5,935,779 | A | 8/1999 | Massey |
| 6,699,724 | B1 | 3/2004 | West et al. |
| 6,887,430 | B1 | 5/2005 | Dou et al. |

FOREIGN PATENT DOCUMENTS

| | | | |
|---|---|---|---|
| EP | 0579292 | * | 1/1994 |

OTHER PUBLICATIONS

Aubry M. et al. "Monoclonal antibodies as probes for the transmembrane structure of neutral endopeptidase 24.11 {'enkephalinase'}" Biochimica et Biophysica Acta, 967 (1988) 56-64.*

Wang W. "Lyophilization and development of solid protein pharmaceuticals" International Journal of Pharmaceutics 203 (2000) 1-60.*

Mejia Expression of an *Onchocerca* vo/vu/us Ov33 homolog in Diro fila ria irn mitis: potential i n i m m u nod i ag n 0s is of heartworm infection Parasite Immunology, 1994 16 297-303.*

Xu et al (Clinica Chimica Acta 325:127-131, 2002).*

Kaur et al (Environmental Science & Technology 41:5028-5036) 2007.*

Cedervall et al (PNAS 104:2050-2055, 2007).*

Medintz et al (Nature Materials 5:581-589, 2006).*

Gates et al (Langmuir 24:4107-4113, Mar. 7, 2008).*

WO2010/006201A3, International Search Report and Written Opinion, Mar. 15, 2010, Abaxis, Inc.

P. Englebienne, A. Van Hoonacker, and J. Valsamis, "Rapid Homogeneous Immunoassay for Human Ferritin in the Cobas Mira Using Colloidal Gold as the Reporter Reagent," Clin. Chem. 46:12, 2000 (2000).

J. Chandler, N. Robinson and K. Whiting, "Handling false signals in gold-based rapid tests." IVDT (2001).

G. V. K. Gasparyan, "Hen egg immunoglobulin Y in colloidal gold agglutination assay: comparison with rabbit immunoglobulin," J. Clin. Lab. Anal. 19:3,124 (2005).

Z. Jiang, S. Sun, A. Liang, W. Huang, and A.Qin, "Gold-Labeled Nanoparticle-Based Immunoresonance Scattering Spectral Assay for Trace Apolipoprotein AI and Apolipoprotein B," Clin. Chem. 52:7, 1389 (2006).

C. Guarise, L. Pasquato, V. D. Filippis and P. Scrimin., "Gold Nanoparticles-based Protease Assay," Proc. Natl. Acad. Sci. 103:11, 3978-3982 (2006).

R. K. Mehra, J. R. Garey, T. R. Butt, W. R. Gray and D. R. Winge, "*Candida glabrata* Metallothioneins: Cloning and sequence of the genes and characterization of proteins" The Journal of Biological Chemistry, 264:33, 19747-19753 (1989).

R. K. Mehra and P. Mulchandani, "Glutathione-mediated transfer of Cu(I) into phytochelatins," Biochem J. 307, 697-705 (1995).

R. K. Mehra, J. Miclat, V. R. Kodati, R. Abdullah, T. C. Hunter and P. Mulchandani, Optical spectroscopic and reverse-phase HPLC analyses of Hg(II) binding to phytochelatins, Biochem J. 314, 73-82 (1996).

C.V. Smythe, "The reaction of iodoacetate and of iodoacetamide with various sulfhydryl groups, with urease, and with yeast preparations," Biological Chemists 114 (1936).

* cited by examiner

*Primary Examiner* — Mary E Mosher
(74) *Attorney, Agent, or Firm* — Cooley LLP

(57) ABSTRACT

The present invention discloses methods of reducing non-specific interactions of interfering species present in a sample in metallic nanoparticle-based assays, thereby increasing the sensitivity of these assays. In particular, the methods entail neutralizing the chemical reactivity of functional groups present in interfering species by addition of a neutralizing agent, such as an alkylating agent or heavy metal ion. The methods are especially useful in assays for the detection of analytes in biological samples. Reagent kits and assay mixtures for the practice of the described methods are also disclosed.

37 Claims, 2 Drawing Sheets

METHODS OF REDUCING NON-SPECIFIC INTERACTION IN METAL NANOPARTICLE ASSAYS

This application claims priority to U.S. Application No. 61/079,777, filed on Jul. 10, 2008, the contents of which are incorporated herein by reference.

BACKGROUND OF THE INVENTION

Accurate detection of analytes in solutions, particularly biological fluids, is critical in several fields, including medical diagnostics, veterinary diagnostics, and food and drug safety. The innate turbidity of complex biological samples, such as blood, plasma, serum, urine, and bile, has made it difficult to develop reliable assays and devices for multiple analytes. Matrix-related interference as well as scattering of light by biocolloids hamper sensitive determinations of analytes where measurements are primarily restricted to turbidity.

Various types of qualitative and quantitative detection assays have been developed for several analytes based on the phenomena of surface plasmon resonance (SPR) and localized surface plasmon resonance (LSPR). SPR occurs in metallic surfaces when surface plasmons are excited. The phenomenon is characterized by a graded reduction in the intensity of the reflected light due to the molecular thickness of the metal surfaces when incident light strikes the surface at a certain angle. LSPR is a similar phenomenon observed in mono-dispersed metallic nanoparticles. The collective oscillations of the surface plasmons result in wavelength selective absorption and scattering of the incident radiation.

Binding of substances, like macromolecules, to the metallic surface or to binding partners absorbed onto the metallic surface can be detected by changes in the local refractive index manifested as shifts in the absorbance spectra. Such assays are incredibly sensitive due to the nature of the interaction of the surface plasmons and the boundary between the metallic surface and the neighboring medium (e.g. air or water). The drawback of using LSPR for detecting a specific analyte in biological samples has always been interference due to non-specific reaction. The opportunity for non-specific interactions in biological samples is particularly high because of macromolecules present in the sample matrix. Such non-specific interactions can result in an incorrect estimation of the concentration of analyte and even false positives. Therefore, it would be desirable to develop methods for reducing or eliminating non-specific interactions from components in sample matrices, especially biological sample matrices, in detection assays based on SPR or LSPR.

SUMMARY OF THE INVENTION

The present invention is based, in part, on the discovery that neutralizing agents can be used to reduce non-specific binding or interaction in assays, e.g., based on SPR. Accordingly the present invention provides methods of reducing non-specific interactions of sample components with metallic nanoparticle surfaces in nanoparticle-based or SPR based detection assays. Such methods are particularly useful for reducing the occurrence of false positives in the detection of analytes in samples, especially complex biological samples.

In one embodiment of the invention, the method comprises mixing a neutralizing agent with a detectable reagent and a test sample, wherein said neutralizing agent reduces the chemical reactivity of one or more interfering species present in the test sample. In another embodiment, the neutralizing agent reduces the reactivity of thiol, amino, imido, seleno, or carboxyl functional groups present in one or more interfering species. The neutralizing agent may be an alkylating agent, heavy metal ion, or any agent that reduces spectral and electrochemical changes of the detectable reagent produced by interfering species present in a sample. In some embodiments, the sample is a biological sample. In other embodiments, the interfering species comprises one or more macromolecules present in the biological sample that exhibit a non-specific binding affinity to the detectable reagent.

In another embodiment of the invention, the detectable reagent is a first binding partner coupled to a metallic nanoparticle. Metallic nanoparticles may include gold particles, silver particles, copper particles, platinum particles, composite particles, gold hollow spheres, gold-coated silica nanoshells, and silica-coated gold shells. In another embodiment, the first binding partner is an antibody. In yet another embodiment, the test sample comprises a second binding partner, wherein said first binding partner forms a complex with said second binding partner. In still another embodiment, the second binding partner is an antigen. The antigen may be an agent that causes a disease or infection in an animal or human, such as a bacteria or virus.

The present invention also provides a reagent kit useful for minimizing non-specific interactions of interfering species present in a sample. In one embodiment, the reagent kit comprises an isolated binding partner coupled to a metallic nanoparticle; a neutralizing agent; and instructions for using the reagents in an assay to minimize non-specific interactions. In another embodiment, the neutralizing agent reduces the chemical reactivity of one or more interfering species that are capable of binding to the metallic nanoparticle. In another embodiment, the neutralizing agent is an alkylating agent. In still another embodiment, the neutralizing agent is a heavy metal ion, wherein the heavy metal ion is preferably a different metal than the metallic nanoparticle.

In some embodiments, the reagent kit may contain one or more additional components. In one embodiment, the reagent kit further comprises a blocking agent, such as bovine serum albumin. In another embodiment, the reagent kit further comprises a sugar. In another embodiment, the reagent kit further comprises a detergent. One or more components of the kit may be formulated as a dry powder or lyophilized. In one embodiment, one or more components are supplied in separate compartments or containers.

The reagent kit may be employed in assays for detecting an analyte in a biological sample. In some embodiments, the analyte may be an antigen from an agent that causes a disease or infection in an animal or human. In other embodiments, the isolated binding partner coupled to a metallic nanoparticle is an antibody that specifically binds to an analyte in a biological sample.

The present invention also contemplates an assay mixture comprising a neutralizing agent; a detectable reagent; and a biological sample. In one embodiment, the neutralizing agent is an alkylating agent. In another embodiment, the neutralizing agent is a heavy metal ion. In another embodiment, the detectable reagent is an antibody coupled to a metallic nanoparticle. The assay mixture increases the sensitivity of metal nanoparticle-based assays for the detection of an analyte in a sample by reducing the non-specific interactions of the metal nanoparticles with interfering species present in the sample.

DETAILED DESCRIPTION OF THE INVENTION

Figure 1:
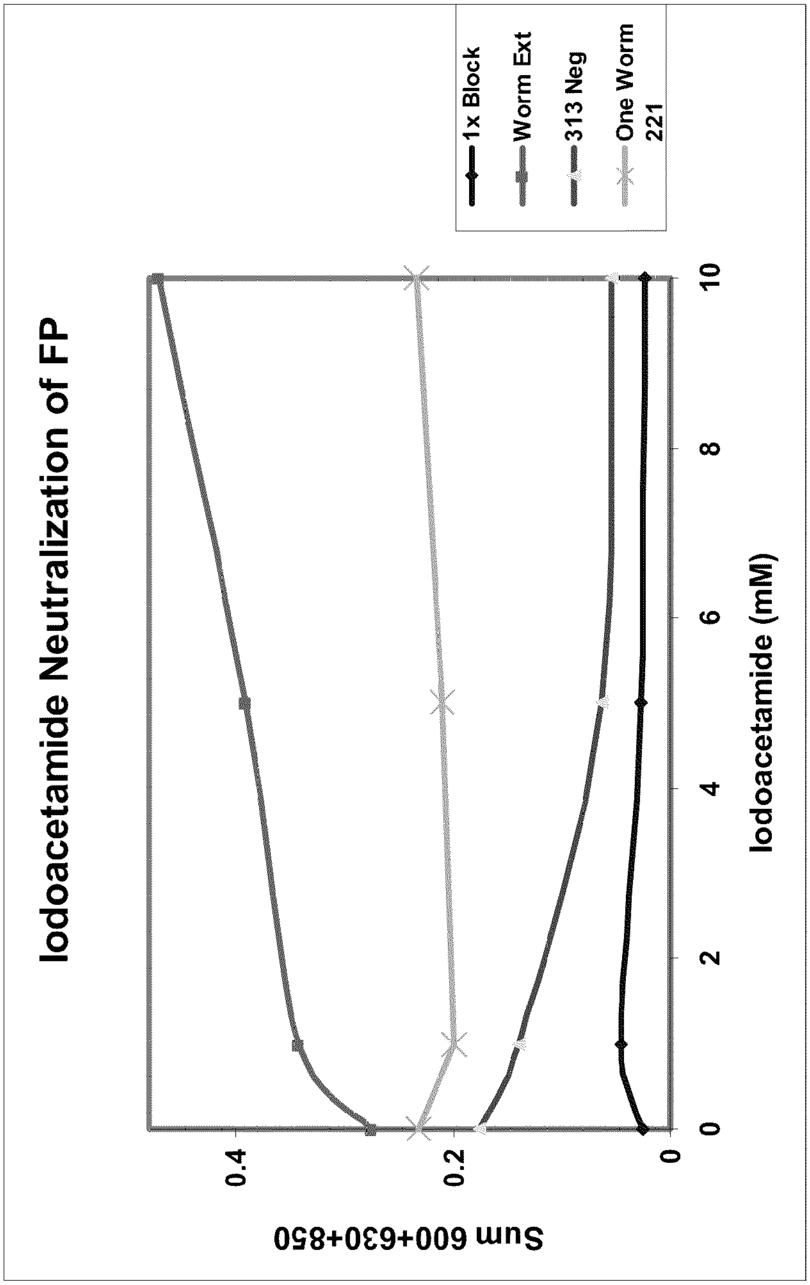
FIG. 1 shows the sums of absorbance values (600, 630 and 850 nm) for each of four samples plotted against iodoacetamide concentration for a homogenous canine heartworm gold-nanoparticle immunoassay.

Detection assays based on the principles of local surface plasmon resonance, which utilize metallic nanoparticles as the detector element, allow for high sensitivity and accurate measurements. However, use of such assays for detecting analytes in complex biological samples has been fraught with problems. These problems arise from components present in the sample matrix binding to the metallic nanoparticle surface resulting in non-specific spectral or electrochemical changes, thus giving rise to false positives and inaccurate analyte concentrations.

The present invention provides methods of reducing non-specific interaction of interfering species present in a sample with a detectable reagent, such as binding partners labeled with metallic nanoparticles, by neutralizing the chemical reactivity of potentially interfering sample components. In one embodiment of the invention, the method comprises mixing a neutralizing agent with a detectable reagent and a test sample, wherein said neutralizing agent reduces the chemical reactivity of one or more interfering species present in the test sample.

A "detectable reagent" is a reagent labeled with an entity that exhibits wavelength selective absorption in the ultra-violet, visible, or near infrared electromagnetic spectrum and scatters incident radiation. Detectable reagents suitable for use in the methods of the present invention include binding partners conjugated to metallic nanoparticles and metal nanoshells. Various types of metallic nanoparticles that may be conjugated to biological macromolecules to form a detectable reagent include, but are not limited to, gold particles, silver particles, copper particles, platinum particles, composite particles, and gold hollow spheres.

Additionally, metal nanoshells as described in U.S. Pat. No. 6,699,724, which is herein incorporated by reference in its entirety, can also be used as the labeling particles. Metal nanoshells are particles comprised of a dielectric core and a metallic coating that have a defined core radius to shell thickness ratio. The core can be comprised of a variety of materials including silicon dioxide, gold sulfide, titanium dioxide, and polystyrene. Suitable metals for the shell include gold, silver, copper, platinum, palladium, lead, and iron. Gold-coated silica nanoshells or silica-coated gold shells are preferred in some embodiments. Binding partners that may be conjugated to metal nanoparticles or nanonshells to form detectable reagents include macromolecules, such as nucleic acids, polynucleotides, antibodies, antigens, receptors, ligands, proteins, and peptides.

In some embodiments, the detectable reagent is an antibody coupled to a metallic nanoparticle.

Methods of conjugating metal nanoparticles or metal nanoshells to macromolecules are well known in the art. One possible method is by passive adsorption. This method involves adjusting the pH of the metal colloid solution to a pH at which the protein to be labeled has a positive charge, mixing the metal colloid solution with the protein solution, and centrifuging the resultant mixture. The labeled protein is then obtained by removing the supernatant and resolubilizing the precipitate. Other methods of conjugating macromolecules to metal nanoparticles or nanoshells are known to the skilled artisan, who can select the proper method based on the type of desired nanoparticle to be used and the type of macromolecule to be labeled. Alternatively, various commercial sources, such as Arista Biologicals (Allentown, Pa.), BioAssay Works, L.L.C. (Ijamsville, Md.), and British Biocell International (Cardiff, United Kingdom) provide metallic nanoparticle conjugates.

The methods of the present invention may be used in virtually any assay in which metallic nanoparticles or metal nanoshells are used as a detector element, including assays employed to identify binding partners of known molecules, detection of particular biological complexes, and assays to detect specific analytes in solution. Formation of various types of complexes may be detected and quantified using the methods of the present invention. Such complexes include, but are not limited to, DNA/DNA, DNA/RNA, RNA/RNA, nucleic acid/protein, receptor/ligand, and antigen/antibody complexes.

As used herein, a "neutralizing agent" is an agent that reduces the chemical reactivity of at least one interfering species. An interfering species may be a biological molecule or other compound present in a solution that exhibits a non-specific binding affinity to the detectable reagent. Biological molecules include, but are not limited to, sterols, hormones, vitamins, and macromolecules, such as lipids, phospholipids, glycolipids, nucleic acids, proteins, polysaccharides, polypeptides, polynucleotides, and carbohydrates. In some embodiments of the invention, one or more interfering species comprises one or more macromolecules that exhibit a non-specific binding affinity to the detectable reagent.

Biological molecules contain various functional groups that are chemically reactive and able to form one or more types of chemical bonds with metallic nanoparticles or metal nanoshells. For example, metallic nanoparticles contain a layer of negative ions adsorbed onto their surface. Any biological molecules that contain a net positive charge will be attracted to the negative ion layer surrounding the metallic nanoparticle surface. In addition, any biological molecules having hydrophobic regions that are in close proximity to the metallic nanoparticles can strongly bind to the hydrophobic metal surface of the nanoparticle. Dative bonds can form between biological molecules having free sulfur groups and the surface of metallic nanoparticles, in particular gold nanoparticles. These types of interactions are, in part, the cause of non-specific interactions of interfering species in a sample, especially a biological sample, and the detectable agent in metallic nanoparticle assays.

In one embodiment, the neutralizing agent reduces the reactivity of at least one functional group present in a biological molecule or interfering species. The functional group may include a thiol or sulfhydryl group, an amino group, an imido group, a seleno group, a carboxyl group, or any other functional group that reacts with metallic surfaces. A neutralizing agent can also refer to an agent that reduces the interaction of at least one biological molecule or interfering species with a metallic surface. A "reduction in interaction" means a decrease in binding of an interfering species to the metallic surface or a reduced effect of the interfering species on the spectral or electrochemical properties of the metal.

In one embodiment of the invention, the neutralizing agent is an alkylating agent. An alkylating agent is an agent that transfers an alkyl group to another molecule. Various functional groups are amenable to receiving an alkyl group. For example, proteins can be alkylated on the free thiol groups of cysteine and methionine residues. Alkylation may also occur on histidine residues and free epsilon amino groups, such as found in lysine residues. Alkylation of nucleic acid molecules can occur on free amino groups of the nitrogen bases, particularly guanine Alkylation of functional groups reduces their chemical reactivity and their propensity to interact with metallic surfaces. By way of example, alkylation of free thiol and amino groups, two functional groups commonly found in biological molecules, prevents dative bonding and charge attraction, respectively to a metallic surface. Alkylating agents suitable for use in the methods of the invention include, but are not limited to, iodoacetamide, iodoacetate, N-ethylmaleimide, PEG-maleimide, ethlymethanesulfonate, 4-vinylpyridine, nitrogen mustards, nitrosourea compounds, dacarbazine, and temozolomide. In a preferred embodiment, the alkylating agent is iodoacetamide.

In another embodiment, the neutralizing agent is a heavy metal ion. Heavy metal ions bind strongly to oxygen, sulfur and nitrogen atoms, and thus can interact with various functional groups comprising these atoms, especially thiol groups. In fact, eukaryotic cells react to elevated concentrations of metal ions in their environment by synthesizing cysteine-rich polypeptides, such as metallothioneins, glutathione, and phytochelatins, and sequestering the metal ions in complexes comprising these polypeptides. Binding of chemically reactive functional groups present in biological molecules or other interfering species by heavy metal ions prevents these interfering molecules from binding to the surfaces of metallic nanoparticles or metal nanoshells found in the detectable reagent. Non-limiting examples of heavy metal ions suitable for use in the methods of the invention include Hg (II), Ag (I), Bi (III), Cu (I), Cu (II), Cd (II), Zn (II), Pb (II), Pt (I), Pt (IV), Au (I), and Au (III). Preferably, the heavy metal ion used as the neturalizing agent is a different metal than that of the metallic nanoparticle or nanoshell used in the detectable reagent.

It is preferable that the neutralizing agent is present in a concentration that substantially reduces or eliminates non-specific interactions of interfering species with the detectable reagent. A "substantial reduction" is at least about 20%, 30%, 40%, 50%, 60%, 70%, 80%, 90%, 95%, or about 99% reduction in interaction of interfering species with the detectable reagent as compared to the interaction that would occur in the absence of the neutralizing agent. Reduction in interaction of interfering species with the detectable reagent may be measured by monitoring changes in absorbance spectra of the detectable reagent in a biological sample matrix in the presence and absence of the neutralizing agent. Optimal concentrations of the neutralizing agent will depend on the particular neutralizing agent, the nature of the detectable reagent (e.g. type of metal nanoparticle or metal nanoshell coupled to the binding partner), and the specific type of biological sample. Suitable final concentrations of the neutralizing agent may be from about 0.1 mM to about 100 mM, preferably from about 0.5 mM to about 50 mM, and more preferably from about 1 mM to about 10 mM. One of ordinary skill in the art would be able to ascertain the appropriate concentration of neutralizing agent for the desired application.

The methods of the invention can be used for reducing or eliminating non-specific interactions of interfering species with a detectable reagent in any type of test sample. The inventive methods are particularly useful for reducing or eliminating non-specific interactions of interfering species in a biological sample, such as blood, plasma, serum, urine, bile, cerebrospinal fluid, and saliva. As discussed above, biological samples contain several interfering species that have one or more functional groups that interact non-specifically with metallic surfaces. Such interactions can lead to inaccurate analyte detection in assays that employ metallic nanoparticles or metal nanoshells as detectable reagents. Thus, the present invention provides methods that reduce or eliminate the occurrence of false positives in assays for detecting one or more analytes in a biological sample. In one embodiment, the detectable reagent is a first binding partner coupled to a metallic nanoparticle. In another embodiment, the test sample comprises a second binding partner, wherein said first binding partner forms a complex with said second binding partner. In another embodiment, the first binding partner is an antibody. In still another embodiment, the second binding partner is an antigen.

Several different types of analytes may be detected with the methods of the invention, particularly those that are significant in the diagnoses of diseases. In some embodiments of the invention, the presence or absence of the analytes predicts the presence or absence of a disease or infection in animals or humans. Several diseases, such as canine monocytic ehrlichiosis, lyme disease, anaplasmosis, influenza, and Legionnaires' disease could be diagnosed using the detection methods presented herein. Some non-limiting examples of such analytes include eptitopes of heartworm, *Ehrlichia canis, Borrelia burgdorferi, Borrelia afzelii, Borrelia garinii, Anaplasma phagocytophilum*, feline leukemia virus, parvovirus, influenza viral A and B strains, avian influenza virus, respiratory syncytial virus, *Legionella*, adenovirus, Group A *Streptococcus*, and other bacteria or viruses known to cause disease in animals or humans. Other analytes that may be detected include compounds, enzymes, or other proteins that are indicative of a certain physiological state or disease in animals or humans. Such analytes may include liver proteins (e.g. alanine aminotransferase, aspartate aminotransferase, and alkaline phosphatase) compounds indicating renal function (e.g. creatinine, urea, and albumin), pancreatic proteins (e.g. canine pancreatic lipase and pancreatic amylase), or blood serum proteins (e.g. lipoproteins and immunoglobulins). Detection of any antigen/antibody complex in a biological sample can be improved using the methods of the invention.

The present invention also provides a reagent kit for reducing non-specific interactions in metallic nanoparticle assays using the materials described herein. In one embodiment, the reagent kit comprises an isolated binding partner coupled to a metallic nanoparticle; a neutralizing agent; and instructions for using the reagents in an assay to minimize non-specific interactions. The binding partner coupled to a metallic nanoparticle may include a macromolecule, such as a nucleic acid, a polynucleotide, an antibody, an antigen, a receptor, a ligand, a protein, or a peptide. In a preferred embodiment, the binding partner coupled to a metallic nanoparticle is an antibody.

In some embodiments, the reagent kit may further comprise a blocking agent, a sugar, a detergent, or combinations thereof. A "blocking agent" is an agent that prevents the association of proteins present in the sample with the detectable agent and/or analyte. Blocking agents are typically proteins themselves and may include, but are not limited to, bovine serum albumin, casein, gelatin, ovalbumin, gamma-globulins, and IgG from non-immunized animals. Sugars that may be incorporated into the reagent kits of the invention include trehalose, sucrose, glucose, lactose, mannitol, ficoll, maltose, maltodextrins, sorbitol and other sugars that act as suitable lyoprotectants or stabilize proteins at ambient temperatures. Non-limiting examples of suitable detergents that may be included in the reagent kit are tween-20, triton X-100, saponin, zwittergents based on sulfotaines, CHAPS, octyl glucosides, and lauryl sulfates.

Components of the reagent kit may be formulated as a dry powder and reconstituted prior to use with assay buffer or test sample. In some embodiments, the dry powder formulations of the reagents are pressed into pellets. Some of the reagents in the kit may be supplied as a dry powder while others are supplied as a liquid formulation. Dry powder or liquid formulations may comprise individual reagents or combinations of reagents. By way of example, the neutralizing agent and the binding partner coupled to a metallic nanoparticle (i.e. metallic nanoparticle conjugate) may be supplied in separate formulations or may be combined in a single formulation. Alternatively, the metallic nanoparticle conjugate may be supplied in one formulation, while the neutralizing agent, sugar, detergent, and blocking agent may be supplied in a second formulation. Formulations of various reagent combinations are possible for inclusion in the reagent kit and are contemplated by the present invention.

In another embodiment, one or more of the reagent components are lyophilized. Methods of lyophilizing formulations and solutions are well known to those skilled in the art. Typically, the formulation or solution is frozen and subsequently lyophilized under vacuum at ambient temperature, reduced temperature, or cycles of various temperatures to cause the water in the sample to sublimate. The appropriate lyophilization conditions, such as temperature, amount of applied pressure, and duration of drying phase, will depend upon the particular formulation or solution and its composition. Such conditions can be adjusted by the skilled artisan without undue experimentation. As described above, the reagents may be present in separate formulations or present in a single formulation in various combinations prior to lyophilization. In some embodiments, one or more of the reagent components are lyophilized into beads.

In the kit, reagents may be provided in separate vials, ampoules, or containers. Alternatively, one or more reagents may be combined following dry powder formulation or lyophilization into a single vial, ampoule, or container. In some embodiments, the reagent kit comprises a container having a plurality of sealed compartments, in which one or more reagents are supplied in separate compartments.

In another embodiment, the reagent kit includes an insert providing instructions for using the reagents in an assay to minimize non-specific interactions. Such instructions may include information pertaining to any required dilutions of the reagents, appropriate sample volumes to be used, proper storage requirements, and stability of the reagents.

The present invention also contemplates an assay mixture of a test sample, a detectable reagent, and a neutralizing agent as described herein. In one embodiment, the assay mixture comprises a neutralizing agent; a detectable reagent; and a biological sample. The components can be added to the mixture in any order. The assay mixture increases sensitivity of assays that measure spectral or electrochemical changes of the detectable reagent by reducing non-specific interactions of interfering species with the detectable reagent. In some embodiments, the assay mixture is used to detect an analyte present in the biological sample. In other embodiments, the assay mixture is used to detect a complex between a binding partner present in the biological sample and the detectable reagent.

The assay mixture may be used in conjunction with commercial analyzers equipped to detect spectral or electrochemical changes of the detectable reagents. Such commercial analyzers include, but are not limited to, plate readers, Cobas Fara analyzers, Piccolo® xpress analyzers, Vetscan, optic fiber readers, and centrifugal analyzers from Olympus, Hitachi etc. In some embodiments, the assay mixture is used in association with non-instrument based assays or lateral flow assays. In some embodiments, the neutralizing agents disclosed herein is used to reduce non-specific interactions between interfering species present in a sample and detectable reagents in non-instrumented assays, such as strip-based lateral flow immunoassays. The neutralizing agents may be incorporated into one or more components typically used in such assays. For example, the neutralizing agent may be absorbed into the sample pad, included in extraction buffer, or dried on to capture strips.

This invention is further illustrated by the following additional examples that should not be construed as limiting. The contents of all references, patents and published patent applications cited throughout this application, as well as the Figures, are incorporated herein by reference in their entirety.

EXAMPLES

Example 1

Iodoacetamide Reduces Non-Specific Interactions in Gold Nanoparticle Immunoassays Anti-heartworm monoclonal or polyclonal antibodies were conjugated to colloidal gold particles having diameters of 25-50 nm by standard passive adsorption techniques. A conjugate reagent was prepared by mixing adequate quantities of the gold conjugate with bovine serum albumin (BSA), trehalose, and triton x-100 in a Tris-buffered medium of pH 8.

An accelerant reagent was prepared by mixing selected polyethylene glycol, sodium chloride and BSA in a Tris-buffered medium of pH 8. Conjugate reagent and accelerant reagent were mixed in appropriate portions inside a microwell in a microtiter plate. Iodoacetamide was added to the reaction mixture at a final concentration of 0 mM, 1 mM, 5 mM, or 10 mM. The reaction was started by adding a suitable volume of undiluted or appropriately diluted sample. Four different samples were used for this experiment: 1× block, worm extract, sample #313, and sample #221. The 1× block sample was a negative control and contained BSA and sodium chloride. The worm extract was a positive control and contained homogenized canine heartworms. Sample #313 was a serum sample from a dog that was verified to be negative for heartworms, but frequently gave “false positive” results in similar assays. Sample #221 was a serum sample from a dog that was infected with a single heartworm.

Absorbance spectra were acquired for each sample at each of the four different iodoacetamide concentrations at 0, 5, and 10 min after reagent mixing. Previous results had shown that the sum of absorbance values at particular wavelengths provided an accurate measure for distinguishing samples positive for heartworm from those that were negative for heartworm. See co-pending U.S. Provisional Application No. 61/038,324, filed Mar. 20, 2008, which is herein incorporated by reference in its entirety. For this experiment, the sum of absorbance values measured at 600, 630 and 850 nm for each sample were plotted against iodoacetamide concentration (FIG. 1). The results showed that the concentration of iodoacetamide had no effect on the measured absorbance values for the negative control sample, which contained only particular reagent components, suggesting that iodoacetamide did not affect the baseline absorbance spectra of the gold nanoparticle conjugates. The signal was improved with increasing iodoacetamide concentration for both the worm extract and the one worm serum sample (sample #221), although the increase in signal for the latter sample was modest. The absorbance measurement for the negative serum sample (sample #313) decreased with increasing iodoacetamide concentration.

Figure 2:
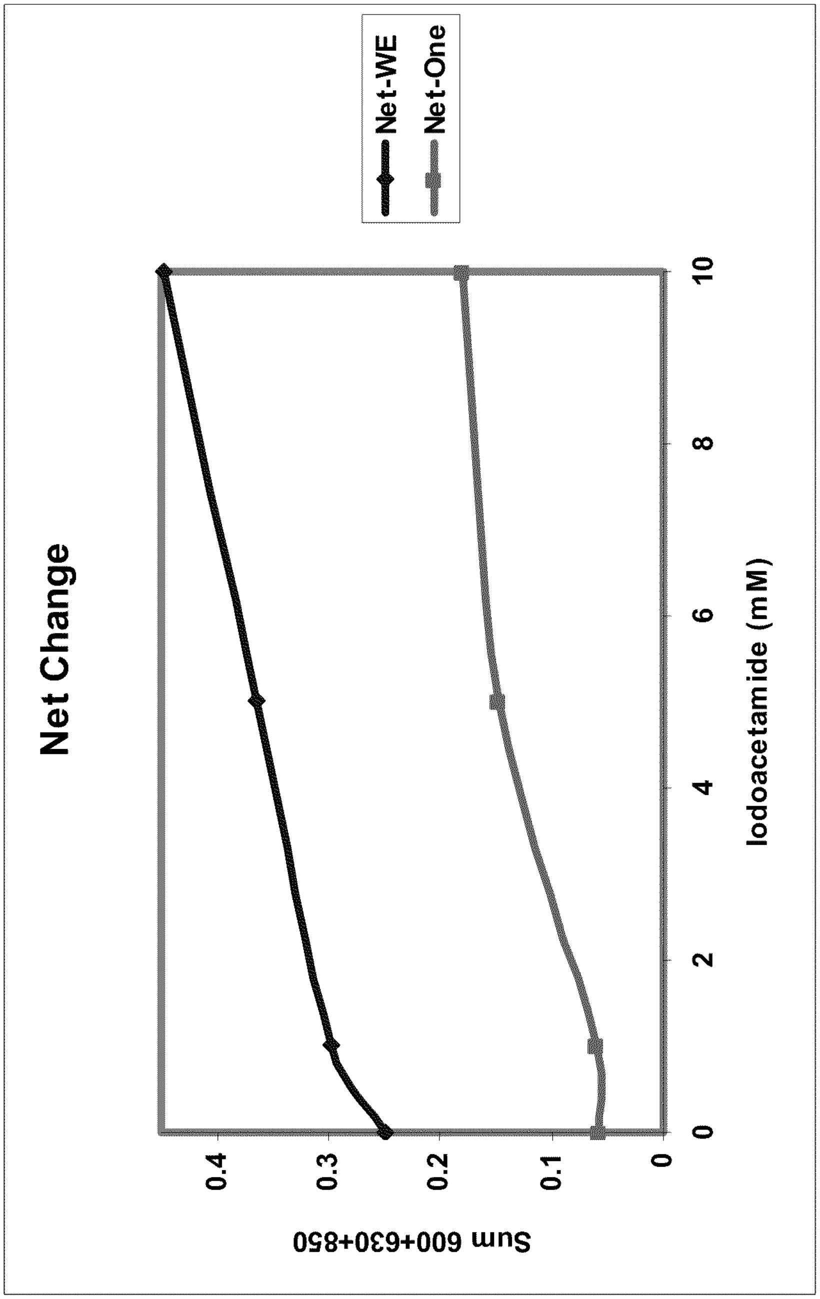
FIG. 2 shows the net absorbance spectra for the worm extract sample and the positive serum sample (sample #221) adjusted for the absorbance values from the corresponding negative samples. Net-WE was obtained by subtracting the absorbance values from the 1× block sample from the absorbance values for the worm extract sample. Net-One was obtained by subtracting the absorbance values from the negative serum sample (sample #313) from the absorbance values for the one worm serum sample (sample #221).

Net absorbance spectra were obtained by subtracting the absorbance values for the negative control sample or the negative serum sample from the absorbance values for the corresponding positive samples. For example, the absorbance values from the 1× block sample were subtracted from the absorbance values from the worm extract sample (Net-WE), while the absorbance values for the negative serum sample (sample #313) were subtracted from the one-worm serum sample (sample #221)(Net-One). FIG. 2 depicts the resulting two net absorbance spectra. The results of this series of experiments suggests that iodoacetamide increases net signals from samples positive for the analyte, canine heartworm in this case. It is also interesting to note that the absorbance values from serum sample #313 (negative for heartworm) were decreased in the presence of iodoacetamide, reducing the likelihood of this sample producing a false positive as it had done previously in similar assays in the absence of iodoacetamide. The increase in net specific positive signals that was observed is likely due to the reduction of non-specific interaction of sample components with the metal nanoparticle surface by iodoacetamide.

It is understood that the disclosed invention is not limited to the particular methodology, protocols and materials described as these may vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. A method of reducing non-specific interaction of interfering species with a detectable reagent comprising:

mixing a neutralizing agent with the detectable reagent and a test sample, wherein the detectable reagent is a binding partner coupled to a metallic nanoparticle or metallic nanoshell, wherein said binding partner specifically binds to an analyte in the test sample; and wherein said neutralizing agent is an alkylating agent or a heavy metal ion that reduces the chemical reactivity of one or more interfering species present in the test sample.

2. The method of claim 1, wherein said neutralizing agent reduces the reactivity of thiol, amino, imido, seleno, or carboxyl functional groups present in one or more interfering species.

3. The method of claim 1, wherein said alkylating agent is selected from the group consisting of iodoacetamide, iodoacetate, N-ethylmaleimide, PEG-maleimide, ethlymethanesulfonate, and 4-vinylpyridine.

4. The method of claim 1, wherein said heavy metal ion is selected from the group consisting of Hg (II), Ag (I), Bi (III), Cu (I), Cu (II), Cd (II), Zn (II), Pb (II), Pt (I), Pt (IV), Au (I), and Au (III).

5. The method of claim 1, wherein one or more interfering species comprises one or more macromolecules that exhibit a non-specific binding affinity to the detectable reagent.

6. The method of claim 1, wherein said test sample is a biological sample.

7. The method of claim 1, wherein said binding partner is a macromolecule.

8. The method of claim 1, wherein said metallic nanoparticle or metallic nanoshell is selected from the group consisting of gold particles, silver particles, copper particles, platinum particles, composite particles, gold hollow spheres, gold-coated silica nanoshells, and silica-coated gold shells.

9. The method of claim 7, wherein said binding partner is an antibody.

10. The method of claim 9, wherein said antibody binds an antigen selected from the group consisting of epitopes of heartworm, canine pancreatic lipase, *Ehrlichia canis, Borrelia burgdorferi, Borrelia afzelii, Borrelia garinii, Anaplasma phagocytophilum*, feline leukemia virus, parvovirus, influenza A strain, influenza B strain, avian influenza virus, respiratory syncytial virus, *Legionella*, adenovirus, and Group A *Streptococcus.*

11. The method of claim 7, wherein said macromolecule is a nucleic acid, a polynucleotide, an antibody, an antigen, a receptor, a ligand, a protein, or a peptide.

12. The method of claim 1, wherein said analyte is an antigen selected from the group consisting of epitopes of heartworm, canine pancreatic lipase, *Ehrlichia canis, Borrelia burgdorferi, Borrelia afzelii, Borrelia garinii, Anaplasma phagocytophilum*, feline leukemia virus, parvovirus, influenza A strain, influenza B strain, avian influenza virus, respiratory syncytial virus, *Legionella*, adenovirus, and Group A *Streptococcus.*

13. A reagent kit comprising:

an isolated binding partner coupled to a metallic nanoparticle or metallic nanoshell, wherein said isolated binding partner specifically binds to an analyte in a biological sample; and a neutralizing agent, wherein said neutralizing agent is an alkylating agent or a heavy metal ion, wherein said isolated binding partner and said neutralizing agent are present in the same formulation.

14. The reagent kit of claim 13, wherein said alkylating agent is selected from the group consisting of iodoacetamide, iodoacetate, N-ethylmaleimide, PEG-maleimide, ethlymethanesulfonate, and 4-vinylpyridine.

15. The reagent kit of claim 13, wherein said heavy metal ion is selected from the group consisting of Hg (II), Ag (I), Bi (III), Cu (I), Cu (II), Cd (II), Zn (II), Pb (II), Pt (I), Pt (IV), Au (I), and Au (III).

16. The reagent kit of claim 13, further comprising a blocking agent selected from the group consisting of bovine serum albumin, casein, gelatin, ovalbumin, and gamma-globulins.

17. The reagent kit of claim 16, further comprising a sugar.

18. The reagent kit of claim 17, further comprising a detergent.

19. The reagent kit of claim 13, wherein the formulation is a dry powder.

20. The reagent kit of claim 13, wherein the formulation is lyophilized.

21. The reagent kit of claim 20, wherein the formulation is in the form of a pellet or a bead.

22. The reagent kit of claim 13, wherein said metallic nanoparticle or metallic nanoshell is selected from the group consisting of gold particles, silver particles, copper particles, platinum particles, composite particles, gold hollow spheres, gold-coated silica nanoshells, and silica-coated gold shells.

23. The reagent kit of claim 13, wherein said isolated binding partner coupled to a metallic nanoparticle or metallic nanoshell is an antibody that specifically binds to an analyte in a biological sample.

24. The reagent kit of claim 23, wherein said antibody binds to an analyte selected from the group consisting of epitopes of heartworm, canine pancreatic lipase, *Ehrlichia canis, Borrelia burgdorferi, Borrelia afzelii, Borrelia garinii, Anaplasma phagocytophilum*, feline leukemia virus, parvovirus, influenza A strain, influenza B strain, avian influenza virus, respiratory syncytial virus, *Legionella*, adenovirus, and Group A *Streptococcus*.

25. An assay mixture comprising a biological sample;

a neutralizing agent, wherein said neutralizing agent is an alkylating agent or a heavy metal ion; and a detectable reagent, wherein said detectable reagent is a binding partner coupled to a metallic nanoparticle or metallic nanoshell, wherein said binding partner specifically binds to an analyte in the biological sample.

26. The assay mixture of claim 25, wherein said alkylating agent is selected from the group consisting of iodoacetamide, iodoacetate, N-ethylmaleimide, PEG-maleimide, ethlymethanesulfonate, and 4-vinylpyridine.

27. The assay mixture of claim 25, wherein said heavy metal ion is selected from the group consisting of Hg (II), Ag (I), Bi (III), Cu (I), Cu (II), Cd (II), Zn (II), Pb (II), Pt (I), Pt (IV), Au (I), and Au (III).

28. The assay mixture of claim 25, wherein said binding partner is an antibody.

29. The reagent kit of claim 13, wherein said isolated binding partner is a macromolecule.

30. The reagent kit of claim 29, wherein said macromolecule is a nucleic acid, a polynucleotide, an antibody, an antigen, a receptor, a ligand, a protein, or a peptide.

31. The assay mixture of claim 25, wherein said neutralizing agent is present in a concentration of about 0.5 mM to about 50 mM.

32. The assay mixture of claim 25, wherein said neutralizing agent is present in a concentration of about 1 mM to about 10 mM.

33. The assay mixture of claim 25, wherein said binding partner is a macromolecule.

34. The assay mixture of claim 33, wherein said macromolecule is a nucleic acid, a polynucleotide, an antibody, an antigen, a receptor, a ligand, a protein, or a peptide.

35. The reagent kit of claim 13, further comprising instructions for mixing the isolated binding partner and the neutralizing agent with a biological sample to minimize non-specific interactions in a detection assay.

36. The assay mixture of claim 25, wherein said metallic nanoparticle or metallic nanoshell is selected from the group consisting of gold particles, silver particles, copper particles, platinum particles, composite particles, gold hollow spheres, gold-coated silica nanoshells, and silica-coated gold shells.

37. The assay mixture of claim 25, further comprising polyethylene glycol.

* * * * *